United States Patent [19]

Ettinger

[11] Patent Number: 4,762,822

[45] Date of Patent: Aug. 9, 1988

[54] REDUCTION OF GASTROINTESTINAL DISEASE-PRODUCING ORGANISMS WITH SIALIC ACID AND GANGLIOSIDES

[76] Inventor: Anna C. Ettinger, 11557 Hartland Rd., Fenton, Mich. 48430

[21] Appl. No.: 763,918

[22] Filed: Aug. 8, 1985

[51] Int. Cl.$^4$ .............................................. A61K 31/70
[52] U.S. Cl. ..................................... 514/25; 514/42; 514/2; 514/23; 514/867; 426/335; 426/532
[58] Field of Search ................... 424/95; 514/25, 42, 514/23, 2, 867; 426/72, 74, 330, 330.2, 335, 532; 536/53, 23

[56]  References Cited

U.S. PATENT DOCUMENTS

| | | | |
|---|---|---|---|
| 4,347,244 | 8/1982 | Mynard et al. | 514/25 |
| 4,447,600 | 5/1984 | Ogura et al. | 536/23 |
| 4,459,286 | 7/1984 | Hilleman et al. | 424/87 |
| 4,476,119 | 10/1984 | della Valle et al. | 514/25 |
| 4,525,459 | 6/1985 | Fletcher | 436/544 |

OTHER PUBLICATIONS

Chem Abs., 100: 154808q, 1984.
Merck Index, 9th Ed., p. 806, No. 6049, 1976.
Chem. Abstrs., 89(25): 212551t, 1978.
Chem. Abstrs., 67(19): 89856n, 1967.
Chem. Abstrs., 80:138986p, 1974.
Chem. Abstrs., 74(22): 122366x, 1971.
Chem. Abstrs., 72(21): 108658w, 1978.
Chem Abstrs., 71(13):59735n, 1969.
*Concise Encyclopedia of Biochemistry*, Walter de Gruyter, New York (1983), pp. 192 and 193.

*Primary Examiner*—John Rollins
*Attorney, Agent, or Firm*—Dressler, Goldsmith, Shore, Sutker & Milnamow, Ltd.

[57]  ABSTRACT

The present invention discloses mother's milk substitutes containing sialic acid or a ganglioside that reduce the number of gastrointestinal disease-producing organisms in a young mammal's food and gastrointestinal tract. The invention also discloses dietary supplements and methods for reducing the number of gastrointestinal disease-producing organisms.

13 Claims, 3 Drawing Sheets

REDUCTION OF GASTROINTESTINAL DISEASE-PRODUCING ORGANISMS WITH SIALIC ACID AND GANGLIOSIDES

TECHNICAL FIELD

The present invention relates to edible products, and particularly to mother's milk substitutes that reduce the number of gastrointestinal disease-producing organisms.

BACKGROUND OF THE INVENTION

Babies fed on mother's milk are known to have fewer medical problems than babies fed mother's milk substitutes. In particular, breast-fed babies suffer fewer infections than babies that are not breast-fed.

In many mammals, mortality is high immediately after parturition and among the newborn. For example, 20 percent of pigs do not survive the first week of life. Approximately one-half of that number die due to gastrointestinal disorders caused by pathogenic strains of one or more bacteria. Further, gastrointestinal disorders contribute to poor growth in many pigs that survive the first week.

The frequency of diarrheal deaths in British infants in 1960 was six times greater for those infants fed cow's milk than those who were breast-fed. [Goldman et al., *J. Pediatr.*, 82:1082 (1979)]In 1979, the incidence of enteric infections was found to be lowest in breast-fed infants in countries where sanitary conditions are poor. [Kabara, Nutrition Reviews, 38:65 (1980)]Whether the above statistics are due to a protective factor in human milk or whether human milk conveys fewer pathogenic organisms has not been determined. [Kabara above; Welsh, *J. Pediatr.*, 94:1 (1979)]

A recent report by Koopman et al., *Am. J. Public Health*, May 1985, compared data on 143 babies with gastrointestinal illness and 143 babies free of such illness. Their case-control study indicated that babies fed on formula were at 6 times the risk of babies on breast milk and 2.5 times the risk of babies on cows'milk.

Among those substances in human milk reported to provide anti-infective properties are a growth enhancer for lactobacillus, an antistaphlococcal agent, immunoglobulins, complement components, lysozyme, lactoperoxidose, lactoferrin, macrophages, lymphocytes and lipids (Kabara, above). However, whether these factors protect the mammary gland from infection or confer infection resistance on the child is unknown (Kabara, above).

The gut of the breast-fed human infant is enriched with lactobacilli in comparison to the gut of infants who are not breast-fed. This difference has been attributed to a lactobacillus growth factor and the high concentration of lactose in human milk, along with its low bulk, low protein content and low buffering capacity. It has been postulated that the high lactose concentration allows sufficient lactose to pass to the intestine to support the growth of lactose fermenters that produce acid conditions and encourage lactobacilli. The large population of lactobacilli alters growth conditions in the gut creating an environment in which diarrhea-producing organisms are less likely to grow (Welsh, above).

Other possible sources of resistance to enteric infections have not been definitively demonstrated. IgA has been thought to be protective (Welsh, above). Complement is thought to be insignificant because human milk heated to 56° C. for thirty minutes retains its antibacterial activity, and that temperature is normally sufficient to inactivate complement.

Studies indicate that milk, particularly human milk, contains lipids thought to account for antimicrobial activity. Data are reported to indicate a strong correlation between microbial resistance and the level of lipase and monoglycerides (Kabara, above). Further, very short chain fatty acids, that is $C_6$ or less, affect gram-negative organisms, the organisms that frequently are responsible for enteric infections.

Kabara et al., *Antimicrob. Aq. Chemother.* 2:23. (1972) advocate adding monoglycerides to improve the lipid formulation of synthetic or animal milk and artificial feeds for human infants and other young mammals to provide the food with more antimicrobial activity as is usually found in human milk.

Kabara et al., above, report several generalities regarding the bacteriostatic activity of fatty acids. Of tested straight chain saturated fatty acids, lauric acid ($C_{12}$) was reported to have the most bacteriostatic activity on gram-positive organisms. Bacteriostatic activity reportedly increased with the addition of one and two double bonds to the fatty acid chain, but a third unsaturation was not as effective. A free carboxyl group was reported to be necessary for activity. Esters reportedly had decreased activity.

However, reduction of the carboxyl group to an aldehyde or alcohol, and changing that group into an amide or amine reportedly increased bacteriostatic effects. Further, in contrast to the other derivatives, amines were active against both gram-positive and gram-negative organisms. Specifically, the addition of monolaurin to milk substitutes and animal feed was advocated to provide the best overall antimicrobial activity.

Investigators have also studied the effect of lipid, and in particular, gangliosides, on the body's response to bacteria or bacterial toxins.

Ganglioside fraction GM1 (monosialoganglioside) is considered to be the cell membrane receptor for heat-labile enterotoxins of *Escherichia coli (E. coli)* and *Vibrio cholerae* [Olsvik et al., *NIPH Ann.*, 6:5, (1983)]. Immunogenicity studies in rabbits indicated that gangliosides inhibited the primary and secondary immune responses to a common bacterial antigen as measured by hemagglutinin levels. However, gangliosides did not inhibit attachment of the antigen to red blood cells or alter the antigenic determinants. Agarwal et al. *J. Immun.*, 107:1448, (1970) concluded gangliosides were an immunosuppressant.

Otaness et al. *Infect. Immun.*, 40:563. (1983) studied the inhibition of *E. coli* and *Vibrio cholerae* enterotoxins by the ganglioside fraction of human milk. They reported that the enterotoxin inhibitor in human milk appeared to be gangliosides, and in particular ganglioside fraction GM1. They concluded that human milk gangliosides may be important in protecting infants against enterotoxin-induced diarrhea at the cell membrane receptor-toxin interaction level, rather than by an effect upon the bacteria themselves.

It would be advantageous to find a substance in human milk that protects the infant from the microorganisms that cause enteric infections, and to use that substance as an additive to milk substitutes for young mammals. It would be particularly desirable to find a relatively more available source of such a substance than human milk that functions protectively in a manner similar to human milk, and that can be added to mother's milk substitutes to enhance the resistance of a young mammal to enteric infections.

SUMMARY OF THE INVENTION

The present invention contemplates an improved food for young mammals comprising a mother's milk substitute that includes sialic acid or a ganglioside present at about 0.005 to 0.1 percent of the total food weight. A preferred sialic acid of this invention is N-acetylneuraminic acid. A ganglioside of this invention is preferably selected from the group consisting of ganglioside fraction GD1a and gangliosides extracted from mammalian brain, human milk, or human colostrum.

The invention also contemplates a dietary supplement comprising a unit dose of an effective amount of sialic acid, ganglioside or a mixture thereof in a physiologically tolerable excipient.

The present invention further contemplates a method for reducing the number of gastrointestinal disease-producing organisms, particularly gram-negative organisms, in the gastrointestinal tract of a mammal, such as a mammalian infant. The method comprises administering about 0.0003 to about 0.02 percent of the mammal's body weight of sialic acid or a ganglioside of this invention to the mammal per day.

The invention still further contemplates a method for reducing the number of gastrointestinal disease-producing organisms, particularly gram-negative organisms, comprising substantially homogeneously admixing about 0.005 to about 0.1 percent of the total food weight of sialic acid or a ganglioside to a mammal's food.

A method for conferring antimicrobial activity on a mother's milk substitute is further contemplated. The method comprises substantially homogeneously admixing sialic acid or a ganglioside of the invention to the mother's milk substitute in an amount of about 0.005 to 0.1 percent of the total weight of milk substitute.

The present invention has several benefits and advantages. One benefit of the present invention is that improved foods in accordance with the invention have bactericidal and bacteriostatic activity against organisms that produce gastrointestinal disease in young mammals.

In third world countries the water with which mother's milk formulae are diluted is frequently contaminated with gastrointestinal disease-producing organisms. Adding sialic acid or a ganglioside of the present invention can reduce the number of disease-producing organisms in the formulae and thus also in the gastrointestinal tract of the child drinking the diluted formulae.

Still further advantages and benefits of the present invention will become apparent to those skilled in the art from the detailed description and examples which follow.

BRIEF DESCRIPTION OF THE DRAWINGS

In the drawings, forming a portion of this disclosure.

The numerals on the upper horizontal axis in the lower row graph labelled "GANGLIOSIDES" indicate the calculated weight of sialic acid in micrograms per 5 milliliters contained within the molecules of the quantity of ganglioside indicated below on the lower horizontal axis. The single numerals on the upper horizontal axis in the lower row graphs labelled GM1 FRACTION, GD1a FRACTION, and GT1 FRACTION indicate the weight percent of each fraction that is constituted by sialic acid.

The graphs labelled "26 PERCENT" and "50 Percent" illustrate assays of the lethal effect of concentrations of sialic acid alone that are equivalent to the amounts contained within ganglioside molecules of a given ganglioside fraction, such as GM1 or GT1, respectively. The horizontal axis indicates the concentration of ganglioside in ug/5ml to which the amount of sialic acid corresponds. The graph labelled "26 Percent" therefore contains 26 percent of the indicated microgram amounts and corresponds to the amount of sialic acid present in the indicated concentrations of GM1 fraction. The graph labelled "50 Percent" corresponds to an intermediate value for the sialic acid content of fractions GD1a and GT1, which are, respectively, 48 and 52 percent sialic acid by weight. The graph illustrates assay values for lethal effects of sialic acid contained in the GD1a and GT1 fractions.

The asterisk (*) indicates the value for the level of presumed significance for the assay values; i.e., 20 percent. Each vertical line represents the assay results of a single representative sample at the indicated concentration. Zeros along the horizontal axes indicate that no bacterial kill was observed for the concentration shown.

Figure 3:
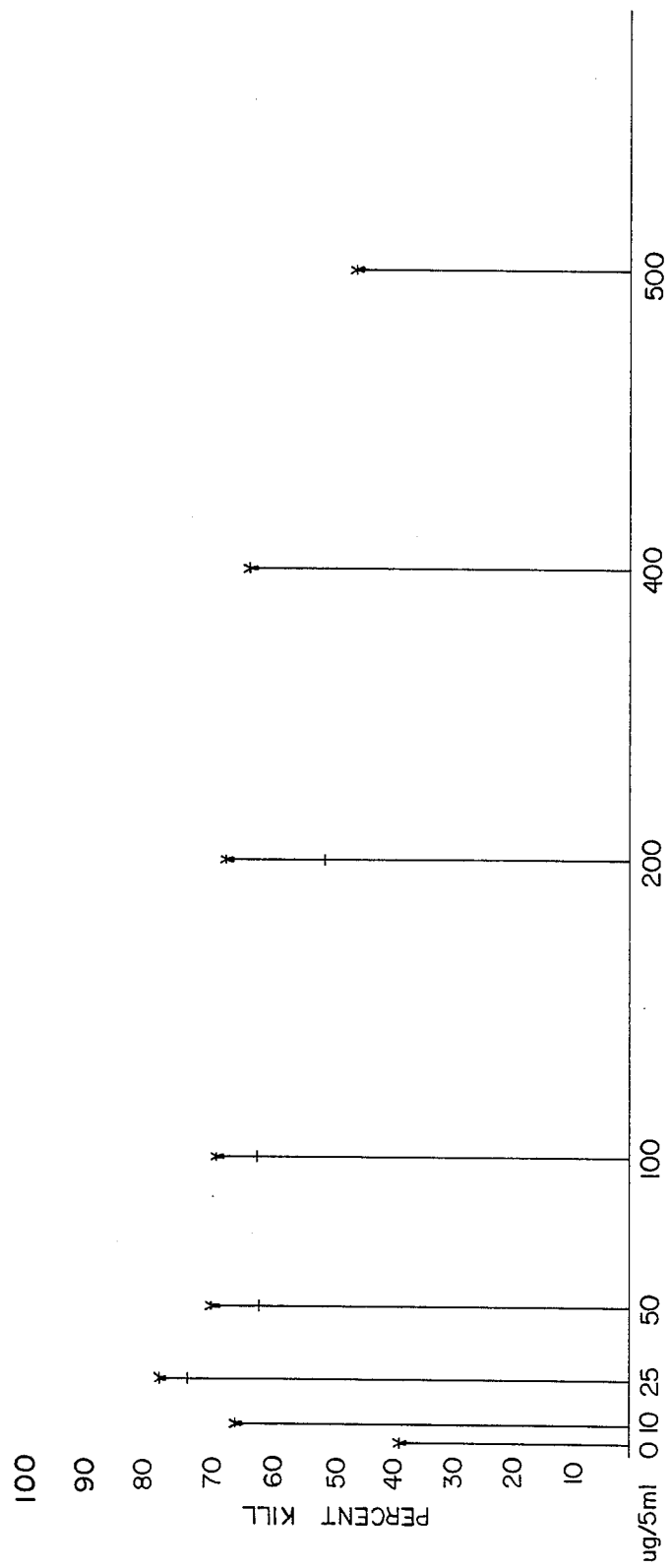

FIG. 3 is a graph that illustrates representative assay results of lethal effects of gangliosides admixed with a commercially available mother's milk substitute formula or nutrient broth on agar plate-cultured E. coli. The asterisk (*) indicates results of assays using a commercially obtained bovine brain ganglioside mixture, and the horizontal bar (-) indicates assay results obtained using human milk gangliosides obtained following the separation scheme illustrated in FIG. 1.

The horizontal axis indicates concentration of homogeneously admixed ganglioside in micrograms per 5 milliliters of formula (ug/5ml). The vertical axis indicates percent E. coli killed relative to zero for control samples.

DETAILED DESCRIPTION OF THE INVENTION

The present invention contemplates an improved food for mammals such as pre-weaned, young mammals that comprises a mother's milk substitute having sialic acid, a ganglioside or a mixture of a sialic acid and a ganglioside present at about 0.01 to about 0.05 weight percent of the total weight of milk substitute composition.

The phrase "young mammal" and its plural are utilized herein to mean mammals such as humans that have not been weaned. The present invention can also be utilized for weaned mammals, but it is believed to be particularly useful for pre-weaned, young mammals.

In a preferred embodiment a ganglioside is present. Gangliosides exhibit antimicrobial activity such as bactericidal and bacteriostatic activity against organisms that are a frequent cause of diarrhea in young mammals. As previously described, bacteria-produced gastrointestinal diseases including diarrhea, flatulence, nausea and vomiting, are a significant cause of death and disease in young mammals. Such diseases are usually caused by gram-negative bacteria.

In human infants this is particularly true in formula-fed babies in third world countries. The water with which a mother's milk substitute such as formula is mixed is frequently contaminated with diarrhea-producing organisms. The child ingests large numbers of these organisms with his/her formula. Such formula-fed infants have much higher levels of morbidity and mortality due to gastrointestinal disease-producing organisms than breast-fed infants.

A preferred ganglioside is the mixture of gangliosides extracted from human milk or colostrum, or that extracted from mammalian brain. A method for extracting gangliosides from human milk or colostrum is described herein in Results Section IA, hereinafter. Substantially the same method can be used on a homogenate of a mammalian brain or other ganglioside containing fluid or tissue.

Gangliosides extracted from bovine brain are most preferred gangliosides of the present invention. Further, bovine brain ganglioside extract is commercially available from, for example, SIGMA CHEMICAL CO. of St. Louis, Mo. Gangliosides from human milk and bovine brain demonstrate similar lethal effects on *E. coli* when substantially homogeneously admixed at similar concentrations in formula, for example.

The results of an assay using a commercially available formula as a physiologically tolerable excipient comparing the lethal effects of various concentrations of bovine brain gangliosides to similar concentrations of human milk gangliosides are illustrated in FIG. 3. That study is described in detail in Results Section III. As can be seen in the FIGURE, ganglioside from human milk or bovine brain have comparable bactericidal and bacteriostatic activity when used at similar concentrations in the commercially available formula or nutrient broth.

Ganglioside fraction GD1a is also a preferred ganglioside of the present invention. Methods for purifying fraction GD1a from gangliosides are well known in the art. The fraction is also commercially available from, for example, SUPELCO, INC. of Bellefonte, Pa.

Also preferred in the present invention is sialic acid. A most preferred sialic acid is N-acetylneuraminic acid (NAN), the sialic acid found in mammalian brain gangliosides. Methods of synthesizing NAN or purifying it from various sources are also well known.

NAN is also available commercially in various forms. For example, NAN is available from SIGMA CHEMICAL CO. of St. Louis, Mo. as a synthetic material, or as extracted from hen's eggs, *E. coli*, human urine, or sheep submaxillary glands.

Figure 2:
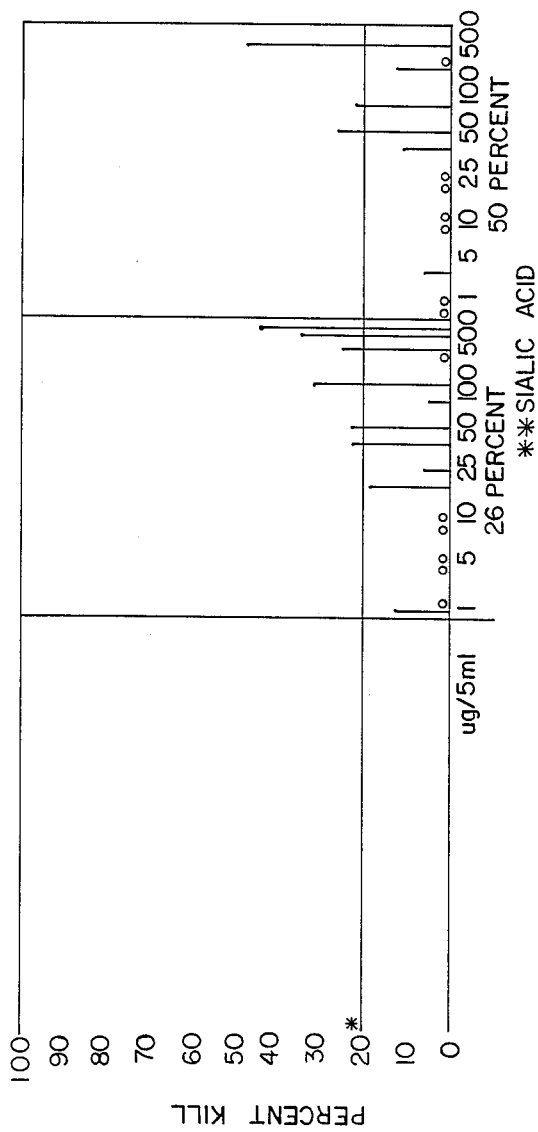
FIG. 2 contains a series of graphs that illustrate the results of assays of the lethal effects of sialic or ganglioside; i.e., sialic acid, and ganglioside fractions GM1, GD1a, and GT1, on agar plate-cultured E. coli. The lower row of graphs illustrates representative assay values of the percentage, relative to control, of E. coli killed by increasing concentrations of gangliosides and ganglioside fractions. The lower horizontal axis represents the concentration of ganglioside in micrograms (ug) per five milliliters (ml) of dietary supplement. The vertical axis represents the percentage of organisms killed relative to a control value set at zero percent.
Figure 2:
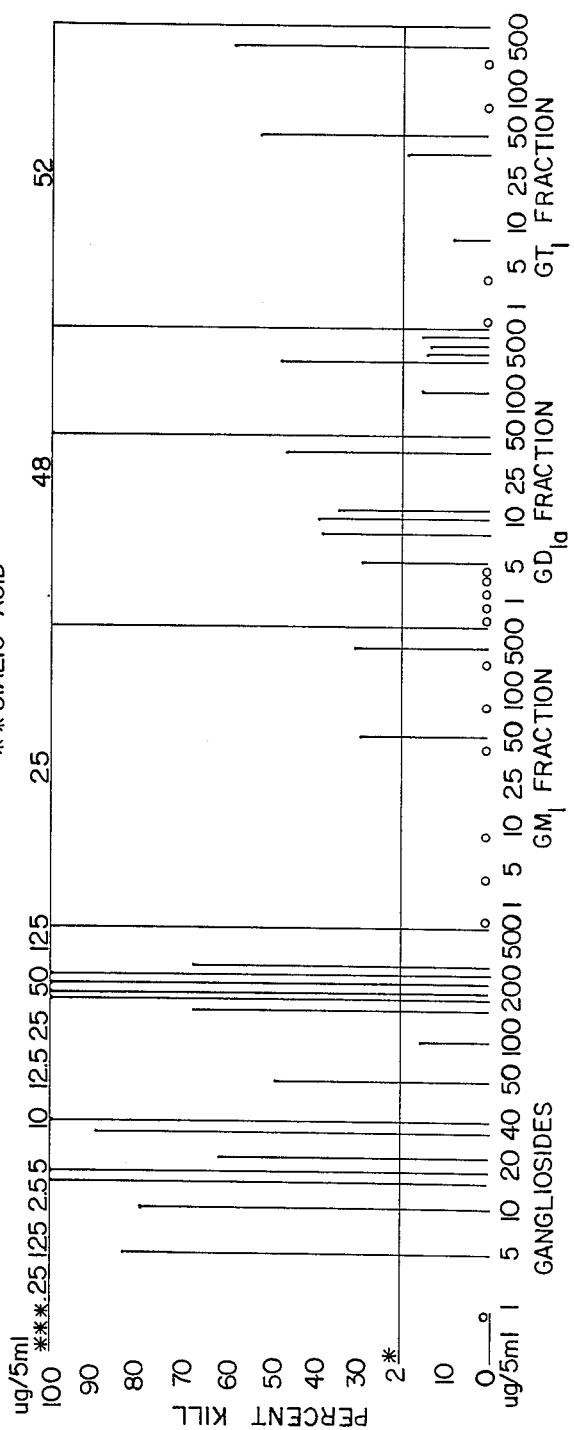

Lethal effects of gangliosides, ganglioside fractions and sialic acid (e.g., NAN) on *E. coli* are illustrated in FIG. 2. The assays are described in detail in Results Section II.

As illustrated in FIG. 2, mammalian brain gangliosides are the most effective bacteriocidal and bacteriostatic agents. However, ganglioside fraction GD1a and sialic acid also demonstrate bactericidal and bacteriostatic activity.

The problems with gastrointestinal disease-producing organisms in humans are generally within the first year of life. Therefore, when the young mammal is a human infant, the mother's milk substitute can be non-human milk, formula or other baby foods prepared for use during the first year or so of the infant's life. Most frequently used non-human milks are bovine and goat.

The most preferred human mother's milk substitute of the present invention is formula, although cow's or goat's milk can also be used. It is preferred to use sialic acid, a ganglioside or a mixture thereof in amount of about 0.005 to about 0.1 percent, and more preferably at about 0.01 to about 0.05 percent, of the total weight of human mother's milk substitute composition.

Human mother's milk substitute formulae typically contain about 90 weight percent water, about 1.5 to about 2.0 weight percent protein, about 6.8 to about 7.2 weight percent carbohydrate, about 3.6 to about 3.8 weight percent fat, and about 0.3 to about 0.4 weight percent minerals, measured as ash. The protein source can be soy isolate or non-fat milk. The carbohydrate can be supplied by, for example, lactose, sucrose, corn syrup, corn starch, or tapioca dextrin. The formulae can also contain additional ingredients such as vitamins.

When the young mammal is a non-human mammal, the preferred mother's milk substitute is feed. In that instance, sialic acid or ganglioside is also substantially homogeneously admixed to be present at about 0.005 to about 0.1 percent, and more preferably about 0.01 to 0.05 percent of the total weight of the feed.

Commercially available feeds that are specifically adapted to the nutritional needs of numerous commercially important mammals are suitable for use in the sialic acid- or ganglioside-containing feeds of this invention. Such feeds are well known and can be obtained from animal feed suppliers.

The sialic acid or ganglioside can be admixed and dispersed in formula, goat's or cow's milk or feed by simple physical mixing procedures. Physical mixing such as homogenization is particularly preferred where cow's and goat's milk are utilized, or where a natural feed such as whole grain particles constitute the feed.

While physical mixing can be utilized for human formulae or processed non-human mammalian feed, it is preferred to admix and disperse the sialic acid or ganglioside, or a mixture thereof, with the formula or a processed feed during its preparation to help assure substantially homogeneous distribution throughout the food. In such instances, the sialic acid, ganglioside or mixture typically constitutes a part of the lipid portion of such foods.

The invention also contemplates a dietary supplement comprising a sialic acid or a ganglioside in a physiologically tolerable excipient. Preferred sialic acids and ganglioside are as previously described.

As an effective amount of sialic acid, ganglioside or a mixture thereof is substantially homogeneously dispersed in the excipient as a unit dose. The effective amount is an amount sufficient to provide about 0.0003 to about 0.02 percent, and more preferably about 0.005 to about 0.015 percent, of the young mammal's body weight per day in the dose form in which the supplement is administered.

Suitable excipients are well known in the art and can be, for example, diluents or binders and adhesives. Diluents are used to expand the volume of materials to constitute a convenient amount of material to compress into a tablet. Exemplary diluents are lactose, starch cellulose, sucrose, dextrose, amylose, and the like. Binders or adhesives are used to add cohesiveness to tablets. Exemplary binders are acacia, tragacanth, sucrose, glucose, gelatin, cellulose, starch and the like.

The purpose of the excipient is to provide sialic acid, ganglioside or mixture thereof in an easily used form. Dosage levels in accordance with the invention are difficult to measure in the household. Therefore, the supplement is preferably provided in an easily measured and administered form. The excipient expands the volume of the sialic acid or ganglioside so that a tablet, or the like, contains sufficient quantities to be added to, for example, a cup of formula or milk.

Further, the excipient can include the young mammal's food. Suitable foods for young mammals are as discussed previously and include animal feeds for non-human mammals and non-human milk, formula and baby foods for human infants. Additional suitable excipients can be those used in tablet making or can be those used to encapsulate the supplement.

The sialic acid and ganglioside of this invention that are suitable are those described as suitable for the improved food for young mammals. N-acetylneuraminic acid, ganglioside fraction GD1a and ganglioside extract are preferred. Most preferred is ganglioside mixture that is an extract of a mammalian brain or human milk or colostrum.

The invention also contemplates a method for reducing the number of microorganisms such as gastrointestinal disease-producing organisms that comprise substantially homogeneously admixing about 0.005 to about 0.1 percent (based on the total weight of the food composition) of sialic acid or ganglioside to a young mammal's food to provide a substantially homogeneous admixture, and maintaining the admixture for a period of time sufficient for sialic acid or ganglioside to contact the organisms and kill them. The admixture of sialic acid or gangliosides with the food reduces the number of gastrointestinal disease-producing organisms such as, for example, $E. coli$ in the young mammal's food.

Further, the reduction of the number of diarrhea-producing organisms in the food can substantially reduce the number of diarrhea-producing organisms in the gastrointestinal tract of the young mammal. This is particularly useful in formulae used in third world countries where sanitary conditions are poor, and adding antimicrobial properties to formulae reduces the number of disease-producing organisms present in the formulae. Reduction of the number of gastrointestinal disease-producing organisms in an infant's formula introduces fewer gastrointestinal disease-producing organisms into the infant's gut. The sialic acid and ganglioside of this invention that are suitable are those described as suitable for the improved food for young mammals.

The invention further contemplates a method for reducing the number of gastrointestinal disease-producing organisms in the gastrointestinal tract of a young mammal that comprises administering to the young mammal about 0.0003 to abut 0.02 percent, more preferably about 0.005 to about 0.015 percent of the young mammal's body weight per day of sialic acid, a ganglioside or a mixture thereof. Exemplary of such organisms are gram-negative bacteria such as $E. coli$ and $V. cholerae$.

The invention also contemplates a method for conferring bactericidal and bacteriostatic activity on a mother's milk substitute that comprises admixing and substantially homogeneously dispersing sialic acid, a ganglioside or their mixture in a mother's milk substitute in an amount of about 0.005 to about 0.1 percent of the total weight of mother's milk substitute.

Mother's milk substitutes are as previously described and include feeds designed for young mammal's nutritional needs and baby foods, non-human milk and formula for human infants.

RESULTS

I. Fractions of Human Milk and Colostrum

Having Bactericidal and Bacteriostatic Activity

A. Fractionation of Human Milk and Colostrum

Figure 1:
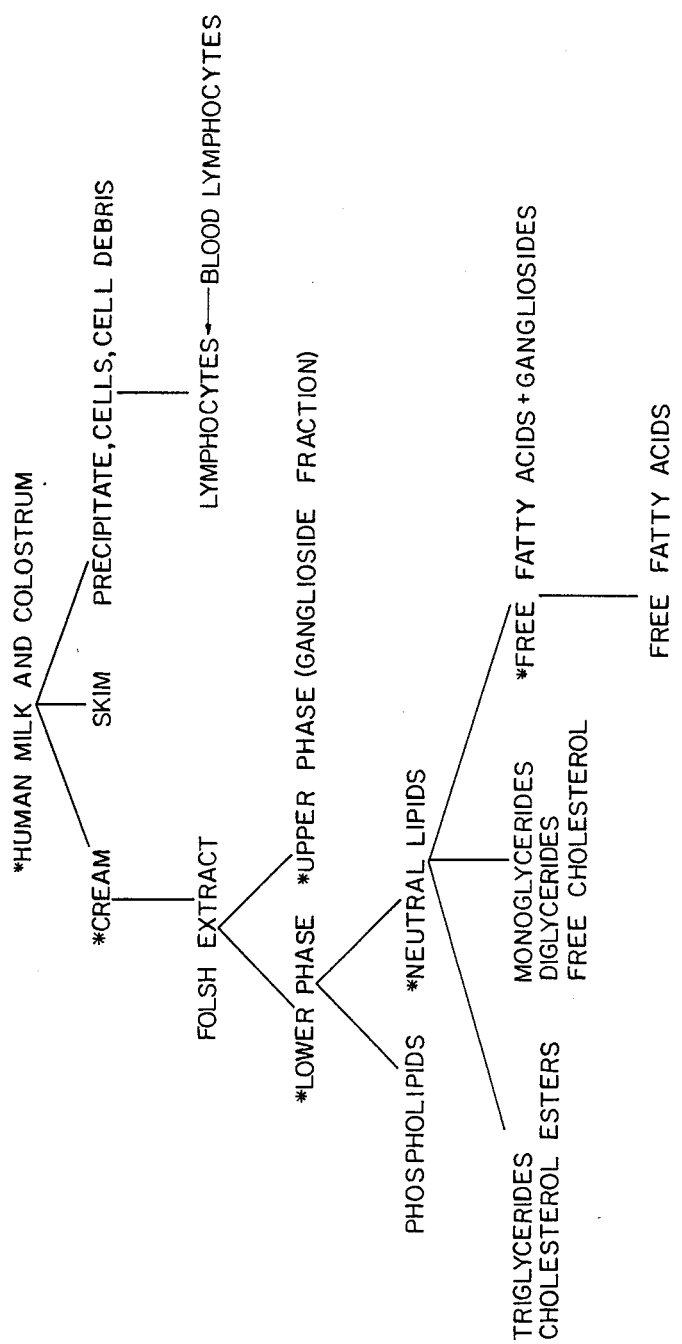
FIG. 1 is a schematic representation showing the fractionation of human milk and colostrum. The asterisk (*) indicates those fractions that exhibited antimicrobial activity upon subsequent assay.

The fractions into which human milk or colostrum were separated are illustrated in FIG. 1.

Initially, samples of human milk or colostrum were collected and separated into three fractions by centrifuging at $700 \times G$ for 1 hour at 4° C. The fractions were precipitate, skim milk or skim colostrum, and cream. Each fraction was spread in a thin layer in a plastic package and exposed to UV light for two hours to kill bacteria that may be present in the fraction. Microscopic examination of each fraction showed that cells were present in the precipitate, with only a few cells remaining in the cream.

Upon subsequent assay (Section C, below), only the cream fraction demonstrated bactericidal or bacteriostatic activity. The cream was further fractionated to determine the components of the cream having bactericidal and bacteriostatic activity.

Total lipids (Folsh extract) were extracted from the ganglioside-containing cream fraction according to the method of Folsh et al., $J. Biol. Chem.$, 226:497 (1957). The method separates lipids into an upper phase ganglioside-containing fraction and a lower phase fraction having neutral lipids and phospholipids.

Briefly, cream was extracted by blending for 1 minute in a Waring blender with 17 volumes of chloroform:methanol (2:1 v/v) followed by filtration. The blender was rinsed with an additional 3 volumes of the chloroform:methanol solution which was admixed with the previous filtrate to form an admixture. Two phases were obtained by shaking the admixture in a separatory funnel with 0.2 volumes of 0.1% NaCl and maintaining the new admixture for a time period of eighteen hours (overnight).

The lower lipid-containing phase of the new admixture was removed and concentrated on a rotary evaporator. The residue was transferred to a volumetric flask with several portions of chloroform:methanol solution. This was labeled Total Lipids (TL). Aliquots of the TL were taken for weight determinations.

The Total Lipids were separated by column chromatography on silicic acid into neutral lipids and phospholipids by the method of Borgstrom, $Acta Physiol. Scand.$, 25:101 (1952). Briefly, the neutral lipid fraction was further separated into three main fractions, triglycerides, monoglycerides, and fatty acids by TLC on silica gel using hexane-chloroform-methanol (73:25:3 v/v/v) [Ferrell et al., $Quart. J. Stud. Alcohol$ 31:810 (1970)]. Each of the main fractions was scraped from the chromatogram, eluted with chloroform, evaporated to dryness under nitrogen, dissolved in chloroform-methanol (1:1 v/v), and subsequently assayed for its ability to inhibit bacterial growth as described herein.

Additionally, lyophilized human milk was extracted using a method developed for the specific isolation of gangliosides [Svennerholm, *Acta Chem. Scand.*, 17:239 (1963)]. The lyophilized milk was extracted with 20 volumes (w/v) of chloroform:methanol (1:2 v/v), and filtered. The filtrate was concentrated using a rotary evaporator and dialyzed for 3 days against cold running tap water. Any lipid which formed was removed and the aqueous ganglioside-containing phase was concentrated on a rotary evaporator. Chloroform:methanol (1:2 v/v) was added to the residue and labeled Ganglioside Extract (GE).

An aliquot of the GE along with standard gangliosides were subjected to thin layer chromatography (Renkonen and Varo, in *Lipid Chromatographic Analysis*, G. V. Marinetti, Ed., Marcel Dekker, N.Y., 1967 pg. 65). After development the plate was sprayed with resorcinol which is specific for sialic acid. (Skipski, in *Methods in Enzymology*, vol. 35 J. M. Lowenstein, Ed., Academic Press, N.Y. 1975, pg. 407).

The results showed the presence of a positive spot with the same mobility as standard ganglioside. An aliquot of the GE was assayed for its ability to inhibit bacterial growth as described hereinafter.

The upper phase was concentrated to dryness in vacuo and was dissolved in chloroform-methanol (1:1 v/v). Thin layer chromatography (TLC) demonstrated a spot with the same mobility as standard gangliosides.

B. Antimicrobial Studies

Non-immunoglobulin antimicrobial factors were found in the cream portion of human milk and colostrum. Upon fractionation of the lipids in the cream these factors were found in the ganglioside fraction of the Folsh extract.

Of the three fractions obtained by TLC of the neutral lipid fraction of the Folsh extract, only the fraction that corresponded in TLC mobility to that of free fatty acids (fatty acid fraction) contained microbiocidal activity.

Additional studies demonstrated that gangliosides and free fatty acids have the same mobility on TLC plates. The fatty acid fraction was treated by acid hydrolysis to destroy ganglioside activity, while not interfering with fatty acids. Following acid hydrolysis, the free fatty acid fraction lost its microbiocidal activity in the assay. The initial bacteriocidal result for the fatty acid fraction was therefore attributed to ganglioside carried-over into the neutral lipid fraction, rather than being due to bactericidal activity of the neutral lipids.

FIG. 1 illustrates the fractions into which milk and colostrum were divided. The asterisk indicates those fractions having antimicrobial activity upon subsequent assay.

C. Assay of Lethal Effect

A bacterial stock culture was prepared by growing *Escherichia coli* 0111 (*E. coli*) in nutrient broth. 24 Hours before the assay the culture was transferred to new broth. Serial dilutions of the stock culture were tested to determine which dilutions produced reliable counts upon plating. Dilutions of $1:10^7$ and $1:10^8$ were used. The stock culture contained about $8 \times 10^8$ to $2 \times 10^9$ *E. coli* per 1 milliliter (ml).

The fractions of the cream of human milk and colostrum were assayed for bacterial growth inhibition in commercially available formulae or nutrient broth.

The formulae used were ENFAMIL and PROSOBEE (Mead Johnson Nutritional Division, Evansville, Indiana), SIMILAC, SIMILAC with iron, and ISOMIL (Ross Laboratories, Columbus, Ohio). The lipid fraction to be assayed was admixed and substantially homogeneously dispersed in 4.9 ml of formula by stirring.

The isolated lipid fractions were similarly assayed by dissolving the fraction in 0.2 ml. of TRITON X-100 [polyoxyethylene (9) nonyl phenyl ether] (Packard Instrument Company, Inc., Downers Grove, IL). The dissolved fraction was brought up to 4.9 ml total volume with nutrrent broth. (3 g Bacto-Beef Extract and 5 g of Bacto-Peptone; Difco Laboratories, Detroit, MI).

Solutions containing up to 4% of TRITON X-100 were studied and determined to have minimal effects on the organism used under the growth conditions of the assay. Further, in studies using broth and detergent, the control tube contained the same concentration of detergent and was used as the 0% kill number to which the samples were compared.

A 0.1 ml aliquot of $1:10^7$ dilution of *E. coli* was added to the lipid fractions in 4.9 ml of formula or broth in a test tube. The contents of each tube were mixed and maintained (incubated) at 37° C. for four hours. Previous studies determined that maintenance intervals of between three and five hours gave consistently reliable results.

After incubation, a 10 microliter (ul) aliquot of each mixture was plated on MacConky agar plates. (Difco Laboratories, Detroit, MI) The plates were incubated at 37° C. for 18 to 24 hours and then colonies of organisms were counted.

II. Lethal Effects of Gangliosides

Ganglioside Fractions, and Sialic Acid

The aforedescribed assay method was used to determine the lethal effects of gangliosides, ganglioside fractions, and sialic acid.

Gangliosides extracted from bovine brain and N-acetylneuraminic acid were purchased from SIGMA CHEMICAL CO. of St. Louis, Missouri. Monosialoganglioside (GM1), disialoganglioside (GD1a), and trisialoganglioside (GT1) were purchased from SUPELCO, INC. of Bellefonte, Pa.

Bovine brain gangliosides and the ganglioside fractions were admixed and substantially homogeneously dispersed in formula at microgram (ug) concentrations ranging from 1 ug/5 ml to 500 ug/5 ml. Bacteristatic and bactericidal activity were measured as described in Section IB.

The level of presumed significance of the assay result was determined by plating numerous replicate aliquots from the same culture tube. The variation between the counts was ±20%.

The graph of FIG. 2 illustrates the results of this study. From three to six or eight replicates of each dilution were studied. A representative value is illustrated on the graph.

As can be seen in FIG. 2, bovine brain gangliosides killed approximately 80% of the organisms at concentrations of 5 ug/5 ml or greater.

The individual ganglioside fractions that were evaluated showed diminished, but useful effects. Of the three individual fractions, GD1a was most effective. Studies of a pool of the three fractions were similar to the results of the GD1a fraction alone.

To determine whether the lethal effect was due to sialic acid contained within the ganglioside molecule, the weight percent of sialic acid in each fraction was calculated. The weight of sialic acid in micrograms per 5 ml corresponding to the weight of sialic acid within the given amount of ganglioside is given along the upper axis of the graph of FIG. 2 of lethal effects of gangliosides. The weight percent of sialic acid within each ganglioside fraction is listed above the graph of the fraction. Thus, N-acetylneuraminic acid comprises 26% of the weight of fraction GM1, 48% of the weight of GD1a and 52% of the weight of GT1.

Solutions of sialic acid containing 26% and 50% of the weight of the ganglioside fractions were similarly diluted, and assayed. As can be seen in FIG. 2, the lethal effect produced by the amount of sialic acid in fraction GM1 did not closely correlate to the lethal effect of the GM1 fraction. Similarly, the amount of sialic acid present in the GD1a and GT1 fractions did not closely correlate to the lethal effect of either fraction.

Both the GD1a fraction and sialic acid are lethally effective on *E. coli*, but neither is as effective as the ganglioside mixture.

III. Lethal Effect of Bovine Brain Gangliosides and Human Milk and Colostrum Gangliosides FIG. 3 shows the comparison between the lethal effects produced by gangliosides extracted from bovine brain, purchased from SIGMA, and gangliosides extracted from human milk and colostrum as previously described in Section IB.

Gangliosides from the two sources were admixed and were substantially homogeneously dispersed in formula to the same concentrations and assayed for their bactericidal and bacteriostatic activities as aforedescribed. As seen in FIG. 3, the activity of gangliosides from bovine brain closely correlates with the activity of gangliosides from human milk.

The foregoing is intended as illustrative of the present invention but is not limiting. Numerous variations and modifications can be effected without departing from the spirit and scope of the novel concepts of the invention. It is to be understood that no limitation with respect to the specific compositions and uses described herein is intended or should be inferred.

What is claimed is:

1. An improved food for young mammals comprising a mother's milk substitute in the form of an animal feed or infant formula having N-acetylneuraminic acid or a ganglioside present at about 0.005 to about 0.1 percent of the total weight of the improved food.

2. The improved food according to claim 1 wherein a ganglioside is present and is selected from the group consisting of mammalian brain ganglioside extract, human milk ganglioside extract, human colostrum ganglioside extract, and ganglioside fraction GD1a.

3. The improved food according to claim 2 wherein the young mammal is a human infant, the mother's milk substitute is infant formula, and ganglioside is present at about 0.01 to 0.05 percent of the weight of the milk substitute.

4. The improved food according to claim 2 wherein the infant formula contains about 90 weight percent water, about 1.5 to 2.0 weight percent protein, about 6.8 to about 7.2 weight percent carbohydrate, about 3.6 to 3.8 weight percent fat and about 0.3 to 0.4 weight percent minerals measured as ash.

5. The improved food according to claim 4 wherein the protein is selected from the group consisting of soy isolate and nonfat milk; the carbohydrate is selected from the group consisting of lactose, sucrose, corn syrup, corn starch, and tapioca dextrin; and said formula additionally contains vitamins.

6. The improved food according to claim 1 wherein the young mammal is a non-human mammal, the milk substitute is animal feed and N-acetylneuraminic acid or a ganglioside is present at about 0.01 to 0.05 percent of the total weight of the feed.

7. A dietary supplement comprising a unit dose of N-acetylneuramine acid or a ganglioside present in an effective amount in a physiologically tolerable excipient.

8. The supplement according to claim 7 wherein a ganglioside is present and is selected from the group consisting of a mammalian brain ganglioside extract and human milk ganglioside extract, human colostrum ganglioside extract and ganglioside fraction GD1a.

9. A method for reducing the number of gastrointestinal disease-producing organisms comprising substantially homogeneously admixing about 0.005 to about 0.1 percent of the total food weight of N-actylneuraminic acid or a ganglioside to a young mammal's food.

10. The method according to claim 9 wherein a ganglioside is present and is selected from the group consisting of mammalian brain ganglioside extract, human milk ganglioside extract, human colostrum ganglioside extract and ganglioside fraction GD1a.

11. The method according to claim 9 wherein the number of gastrointestinal disease-producing organisms in said young mammal's gastrointestinal tract is reduced.

12. A method for conferring antimicrobial activity on a mother's milk substitute in the form of animal feed or infant formula comprising substantially homogeneously admixing N-acetylneuraminic acid or a ganglioside to said mother's milk substitute in an amount of about 0.005 to about 0.1 percent of the total weight of the milk substitute.

13. The method according to claim 12 wherein a ganglioside is present and is selected from the group consisting of mammalian brain ganglioside extract, human milk ganglioside extract, human colostrum ganglioside extract and ganglioside fraction GD1a.

* * * * *

UNITED STATES PATENT AND TRADEMARK OFFICE
CERTIFICATE OF CORRECTION

PATENT NO. : 4,762,822
DATED : August 9, 1988
INVENTOR(S) : Anna C. Ettinger

It is certified that error appears in the above-identified patent and that said Letters Patent is hereby corrected as shown below:

Column 7, line 60 delete "abut" and insert --about--

Column 10, line 8 delete "nutrrent" and insert --nutrient--

Claim 7, line 2 delete "N-acetylneuramine" and insert --N-acetylneuraminic--

Signed and Sealed this

Twenty-first Day of February, 1989

Attest:

DONALD J. QUIGG

Attesting Officer

Commissioner of Patents and Trademarks